(12) United States Patent
Ostapoff et al.

(10) Patent No.: US 9,597,426 B2
(45) Date of Patent: Mar. 21, 2017

(54) HYDROGEL FILLED BARBED SUTURE

(71) Applicant: Covidien LP, Mansfield, MA (US)

(72) Inventors: Roland Ostapoff, East Haven, CT (US); Timothy Sargeant, Guilford, CT (US)

(73) Assignee: Covidien LP, Mansfield, MA (US)

( * ) Notice: Subject to any disclaimer, the term of this patent is extended or adjusted under 35 U.S.C. 154(b) by 695 days.

(21) Appl. No.: 14/148,960

(22) Filed: Jan. 7, 2014

(65) Prior Publication Data
US 2014/0213966 A1 Jul. 31, 2014

Related U.S. Application Data

(60) Provisional application No. 61/756,630, filed on Jan. 25, 2013.

(51) Int. Cl.
| | | |
|---|---|---|
| A61B 17/04 | (2006.01) | |
| A61L 17/00 | (2006.01) | |
| A61B 17/06 | (2006.01) | |
| A61B 17/00 | (2006.01) | |

(52) U.S. Cl.
CPC ...... *A61L 17/005* (2013.01); *A61B 17/06166* (2013.01); *A61B 17/00491* (2013.01); *A61B 2017/00526* (2013.01); *A61B 2017/00884* (2013.01); *A61B 2017/00889* (2013.01); *A61B 2017/00893* (2013.01); *A61B 2017/00951* (2013.01); *A61B 2017/0608* (2013.01);
(Continued)

(58) Field of Classification Search
CPC .... A61B 17/06166; A61B 2017/06176; A61B 2017/00893; A61B 17/00491; A61B 2017/00004; A61B 2017/00951; A61B 2017/06057; A61B 2017/06185; A61B 2017/00495; A61B 2017/00526; A61B 2017/00884; A61B 2017/00889; A61L 17/005

USPC ..... 606/151, 224, 228; 604/93.01; 623/1.42, 623/23.72

See application file for complete search history.

(56) References Cited

U.S. PATENT DOCUMENTS

| | | |
|---|---|---|
| 3,212,502 A | 10/1965 | Myers |
| 3,474,703 A | 10/1969 | Davis et al. |
| 3,791,388 A | 2/1974 | Hunter et al. |

(Continued)

FOREIGN PATENT DOCUMENTS

| | | |
|---|---|---|
| EP | 1 541 181 A1 | 6/2005 |
| GB | 1091669 A | 11/1967 |
| JP | 9-31781 | 2/1997 |

OTHER PUBLICATIONS

Extended European Search Report corresponding to counterpart Int'l Appln. No. EP 14 15 2398.5 dated May 30, 2016.

*Primary Examiner* — Katherine M Shi

(57) ABSTRACT

A medical device includes an elongated body including an outer surface having a plurality of barbs extending therefrom and an inner surface defining a lumen therethrough. The elongated body includes at least one channel extending through the inner surface and the outer surface, the channel defined between an inner surface of one of the plurality of barbs and a cut outer surface of the elongated body. A wound treatment material is disposed within the lumen of the elongated body. The barb is configured to move between a first position to close the channel and retain the wound treatment material within the lumen and a second position to open the channel and permit the release of the wound treatment material therethrough.

19 Claims, 2 Drawing Sheets

(52) U.S. Cl.
CPC ............... *A61B 2017/06057* (2013.01); *A61B 2017/06176* (2013.01); *A61B 2017/06185* (2013.01)

(56) References Cited

U.S. PATENT DOCUMENTS

| | | |
|---|---|---|
| 3,991,766 A | 11/1976 | Schmitt et al. |
| 4,159,720 A | 7/1979 | Burton |
| 4,841,968 A | 6/1989 | Dunn et al. |
| 4,981,149 A | 1/1991 | Yoon et al. |
| 5,480,411 A | 1/1996 | Liu et al. |
| 5,665,109 A | 9/1997 | Yoon |
| 5,735,829 A | 4/1998 | Cherian |
| 6,011,121 A | 1/2000 | Goldmann et al. |
| 6,191,236 B1 | 2/2001 | Roby et al. |
| 6,264,675 B1 | 7/2001 | Brotz |
| 6,551,353 B1 | 4/2003 | Baker et al. |
| 8,221,120 B2 | 7/2012 | Viola |
| 2002/0173770 A1 | 11/2002 | Flory et al. |
| 2005/0070959 A1 | 3/2005 | Cichocki, Jr. |
| 2005/0107738 A1 | 5/2005 | Slater et al. |
| 2005/0125034 A1 | 6/2005 | Cichocki, Jr. |
| 2006/0009801 A1 | 1/2006 | McGurk et al. |
| 2010/0160961 A1 | 6/2010 | Nawrocki et al. |

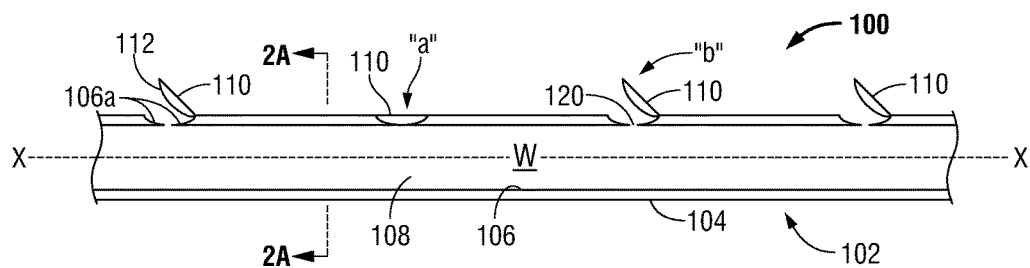
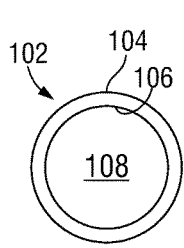
FIG. 2A
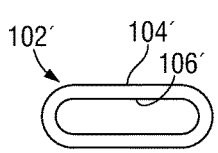
FIG. 2B
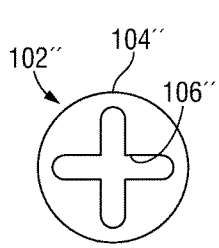
FIG. 2C
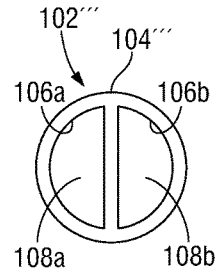
FIG. 2D
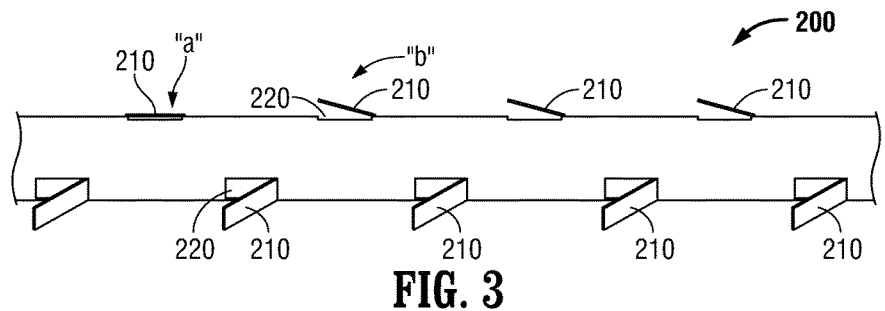
FIG. 3
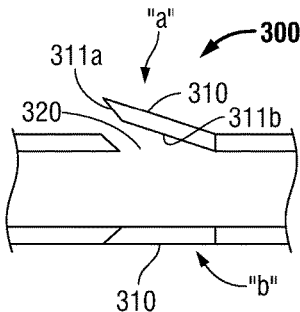
FIG. 4
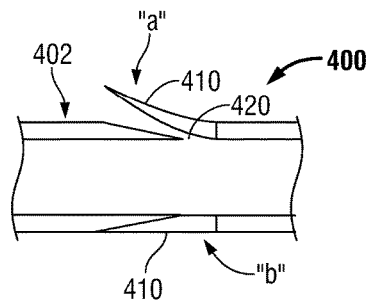
FIG. 5

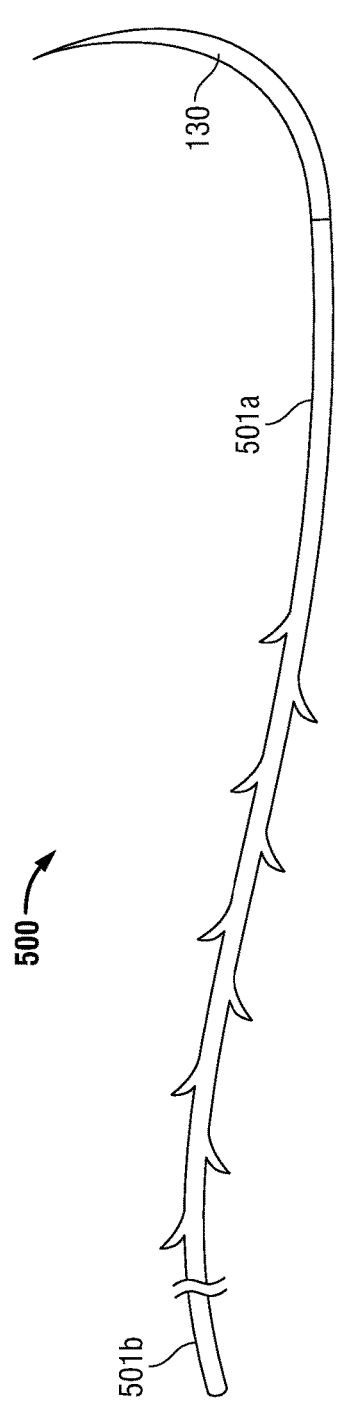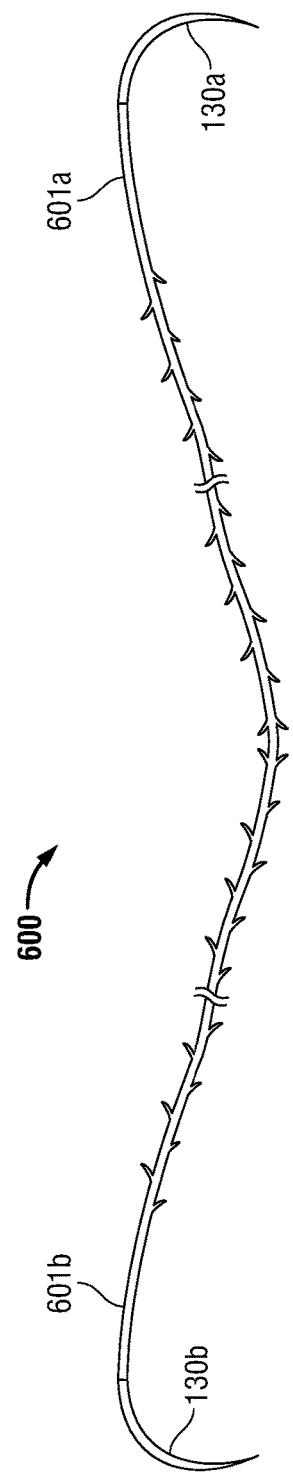

HYDROGEL FILLED BARBED SUTURE

CROSS-REFERENCE TO RELATED APPLICATIONS

This application claims the benefit of and priority to U.S. Provisional Patent Application No. 61/756,630, filed Jan. 25, 2013, the entire disclosure of which is incorporated by reference herein.

BACKGROUND

Technical Field

The present disclosure relates to sutures and methods of forming and using the same, and, more particularly, to barbed sutures containing a wound treatment material.

Background of Related Art

Throughout the years, the medical field has utilized various techniques in an effort to join or bond body tissue together. Historically, suturing was the accepted technique for rejoining severed tissues and closing wounds. Typically, suturing is achieved with a surgical needle and a suture thread. The intended function of sutures is to hold the edges of a wound or tissue against one another during the healing process so as to reduce discomfort, pain, scarring and the time required for healing. Recently, sutures have been replaced or supplemented with adhesives to effect tissue closure, sealants to guard against leakage, hemostats to prevent bleeding, as well as therapeutic agents to aid in healing.

It would be advantageous to provide a barbed suture containing a wound treatment material that may be released therefrom to reduce pain and instances of leakage and/or bleeding, to enhance the healing process, and to create a strong bond between adjacent tissues.

SUMMARY

In accordance with an aspect of the present disclosure, a medical device includes an elongated body including an outer surface having a plurality of barbs extending therefrom and an inner surface defining a lumen therethrough. The elongated body includes at least one channel extending through the inner surface and the outer surface, the channel defined between an inner surface of one of the plurality of barbs and a cut outer surface of the elongated body. A wound treatment material is disposed within the lumen of the elongated body. The barb is configured to move between a first position to close the channel and retain the wound treatment material within the lumen and a second position to open the channel and permit release of the wound treatment material therethrough.

The wound treatment material may be an adhesive, sealant, hemostat, medicament, or a combination thereof. In embodiments, the wound treatment material is a hydrogel. The hydrogel may be used alone or in combination with another wound treatment material.

In accordance with another aspect of the present disclosure, a method of making a barbed medical device containing a wound treatment material disposed within a lumen thereof includes filling a lumen of a medical device with a wound treatment material. The medical device includes an elongated body including an outer surface having a plurality of barbs extending therefrom and an inner surface defining the lumen therethrough. The elongated body includes at least one channel extending through the inner surface and the outer surface, the channel defined between an inner surface of one of the plurality of barbs and a cut outer surface of the elongated body. The barb is configured to move between a first position that closes the channel and retains the wound treatment material within the lumen and a second position which opens the channel and permits the release of the wound treatment material therethrough.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein:

FIG. 1 is a cross-sectional view of a barbed suture containing a wound treatment material in accordance with an embodiment of the present disclosure;

FIG. 2A is a transverse cross-sectional view taken along line 2a-2a of FIG. 1;

FIGS. 2B-2D are transverse cross-sectional views of barbed sutures in accordance with embodiments of the present disclosure;

FIG. 3 is a perspective view of a barbed suture in accordance with another embodiment of the present disclosure;

FIGS. 4 and 5 are cross-sectional views of barbed sutures in accordance with other embodiments of the present disclosure;

FIG. 6 is a perspective view of a unidirectional barbed suture in accordance with an embodiment of the present disclosure; and FIG. 7 is a perspective view of a bi-directional barbed suture in accordance with an embodiment of the present disclosure.

DETAILED DESCRIPTION

A barbed suture including a wound treatment material is described herein. While the present discussion and figures below depict exemplary embodiments of the present disclosure in terms of a monofilament suture, it should be understood that the present disclosure may be utilized in any barbed surgical or medical device for closure of tissue, such as multifilament sutures, ribbons, tapes, meshes, surgical staples, suture anchors, and the like.

A suture of the present disclosure may be formed from any sterilizable biocompatible material that has suitable physical properties for the intended use of the device. The suture may be fabricated from any natural or synthetic, biodegradable and/or non-biodegradable polymeric and/or metallic material that can be used in surgical or medical procedures.

The term "biodegradable" as used herein is defined to include both bioabsorbable and bioresorbable materials. By biodegradable, it is meant that the material decomposes, or loses structural integrity under body conditions (e.g., enzymatic degradation or hydrolysis) or is broken down (physically or chemically) under physiologic conditions in the body such that the degradation products are excretable or absorbable by the body. Absorbable materials are absorbed by biological tissues and disappear in vivo at the end of a given period, which can vary, for example, from hours to several months, depending on the chemical nature of the material. It should be understood that such materials include natural, synthetic, bioabsorbable, and/or certain non-absorbable materials, as well as combinations thereof.

Representative natural biodegradable polymers include: polysaccharides such as alginate, dextran, chitin, chitosan, hyaluronic acid, cellulose, collagen, gelatin, fucans, glycosaminoglycans, and chemical derivatives thereof (substitutions and/or additions of chemical groups include, for example, alkyl, alkylene, amine, sulfate, hydroxylations, carboxylations, oxidations, and other modifications routinely made by those skilled in the art); catgut; silk; linen; cotton; and proteins such as albumin, casein, zein, silk, soybean protein, and copolymers and blends thereof alone or in combination with synthetic polymers.

Synthetically modified natural polymers include cellulose derivatives such as alkyl celluloses, hydroxyalkyl celluloses, cellulose ethers, cellulose esters, nitrocelluloses, and chitosan. Examples of suitable cellulose derivatives include methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxymethyl cellulose, cellulose triacetate, and cellulose sulfate sodium salt.

Representative synthetic biodegradable polymers: poly (lactic acid); poly(glycolic acid); poly(trimethylene carbonate); poly(dioxanone); poly(hydroxybutyric acid); poly(hydroxyvaleric acid); poly(lactide-co-($\epsilon$-caprolactone-)); poly (glycolide-co-($\epsilon$-caprolactone)); polycarbonates; poly (pseudo amino acids); poly(amino acids); poly (hydroxyalkanoate)s such as polyhydroxybutyrate, polyhydroxyvalerate, poly(3-hydroxybutyrate-co-3-hydroxyvalerate), polyhydroxyoctanoate, and polyhydroxyhexanoate; polyalkylene oxalates; polyoxaesters; polyanhydrides; polyester anyhydrides; polyortho esters; and copolymers, block copolymers, homopolymers, blends, and combinations thereof.

Some non-limiting examples of suitable non-degradable materials include: polyolefins such as polyethylene (including ultra high molecular weight polyethylene) and polypropylene including atactic, isotactic, syndiotactic, and blends thereof polyethylene glycols; polyethylene oxides; polyisobutylene and ethylene-alpha olefin copolymers; fluorinated polyolefins such as fluoroethylenes, fluoropropylenes, fluoroPEGSs, and polytetrafluoroethylene; polyamides such as nylon, Nylon 6, Nylon 6,6, Nylon 6,10, Nylon 11, Nylon 12, and polycaprolactam; polyamines; polyimines; polyesters such as polyethylene terephthalate, polyethylene naphthalate, polytrimethylene terephthalate, and polybutylene terephthalate; polyethers; polybutester; polytetramethylene ether glycol; 1,4-butanediol; polyurethanes; acrylic polymers; methacrylics; vinyl halide polymers such as polyvinyl chloride; polyvinyl alcohols; polyvinyl ethers such as polyvinyl methyl ether; polyvinylidene halides such as polyvinylidene fluoride and polyvinylidene chloride; polychlorofluoroethylene; polyacrylonitrile; polyaryletherketones; polyvinyl ketones; polyvinyl aromatics such as polystyrene; polyvinyl esters such as polyvinyl acetate; etheylene-methyl methacrylate copolymers; acrylonitrile-styrene copolymers; acrylonitrile butadiene styrene resins; ethylene-vinyl acetate copolymers; alkyd resins; polyoxymethylenes; polyphosphazine; polyimides; epoxy resins; aramids; rayon; rayon-triacetate; spandex; silicones; and copolymers and combinations thereof.

In embodiments, the suture may include: metals such as steel or titanium; metal alloys including degradable alloys such as iron-based or magnesium-based degradable alloys; and the like.

The suture includes barbs formed along a portion or the entire length thereof in specified or random patterns. Barbs may be formed from angled cuts in an outer surface of a suture. The barbs may all be oriented in the same or different directions, and may be cut at the same or different barb angles. The barbs may be single angle barbs or compound barbs. Single barbs may be formed by a single cut in an inner surface thereof, while compound barbs include an inner surface having at least two cuts disposed at first and second orientations, respectively, relative to a longitudinal axis of the suture. Examples of single and compound barb configurations which may be utilized include those disclosed in U.S. Patent Application Publication No. 2009/0210006, entitled "Compound Barb Medical Device and Method", the entire disclosure of which is incorporated by reference herein.

The barbs can be arranged in any suitable pattern, for example, in a helical pattern around the suture. The number, configuration, and spacing of the barbs can vary depending upon the tissue in which the suture is used, as well as the composition and geometry of the material utilized to form the suture. Additionally, the proportions of the barbs may remain relatively constant while the overall length, number, and spacing of the barbs may be determined by the tissue being connected.

The surface area of the barbs may also vary. For example, fuller-tipped barbs can be made of varying sizes designed for specific surgical applications. When joining fat and relatively soft tissues, large barbs may be desired, whereas smaller barbs may be more suitable for collagen-dense tissues. In some embodiments, a combination of large and small barbs on the same structure may be beneficial, for example, when used in a tissue repair with differing tissue layer structures. A combination of large and small barbs may be used within the same suture such that the barb sizes are customized for each tissue layer to ensure maximum holding properties.

Referring now to the drawings, wherein like reference numerals identify similar or identical elements, FIG. 1 illustrates surgical suture 100. Suture 100 includes an elongated suture body 102 defining a central longitudinal axis "X". Suture body 102 includes an outer surface 104 and an inner surface 106 defining a lumen 108 therethrough. Lumen 108 may extend through a portion or the entire length of the suture body 102.

While suture 100 is shown having a circular cross-sectional geometry in which both outer surface 104 and inner surface 106 are co-axially arranged about longitudinal axis "X', as shown in FIG. 2A, it should be understood that the outer surface and inner surface of the suture body may be of any suitable shape. For example, the outer and inner surfaces 104' and 106' of suture body 102' may be elliptical, as illustrated in FIG. 2B. Other alternate configurations include, for example, square, flat, octagonal, rectangular, as well as eccentric shapes. It is also envisioned that the geometry of the outer surface of a suture body may be different from the inner surface of the suture body. For example, as illustrated in FIG. 2C, outer surface 104" of suture body 102" may be round and inner surface 106" may be eccentric. In some embodiments, as illustrated in FIG. 2D, suture body 102''' may include more than one lumen 108a and 108b, in which the shape of the inner walls 106a and 106b of each of lumens 108a and 108b may be the same as, or different from, each other and the outer wall 104'''.

Referring again to FIG. 1, suture body 102 includes a plurality of barbs 110 extending therefrom. Barbs 110 include an inner surface 112 that corresponds with a cut outer surface 106a of the suture body 102. The cut outer surface 106a of the suture body 102 is an interrupted surface including a channel 120 extending through both the outer surface 104 and the inner surface 106 thereby providing fluid communication between the lumen 108 and the outside environment.

The size of channel 120 is determined by how deeply a barb 110 is cut into the suture body 102. As illustrated, channel 120 may extend only along a portion of the length of the barb. In other embodiments, as illustrated in FIG. 3, channel 220 may extend along the entire length of a barb 210 of suture 200. In yet other embodiments, such as a suture including compound barbs 310 having a first angled portion 311a and a second angled portion 311b, as illustrated in FIG. 4, channel 320 may extend along the length of one of the angled portions, e.g., the second angled portion 311b. In other embodiments, as illustrated in FIG. 5, a channel 420 may be formed at a barb angle formed at the intersection of the single angle barb 410 with the suture body 402. It is envisioned that the barbs and channels may be formed in a variety of configurations, and may be provided uniformly or in different combinations on a suture of the present disclosure.

Needle(s) may be attached to a suture of the present disclosure. As illustrated in FIG. 6, suture 500 is a unidirectional barbed suture including first end 501a that is attached to needle 130 and second end 501b that is free from attachment. Second end 501b may be crimped, bonded, fused, or otherwise joined to close an end of the lumen (not shown). FIG. 7 illustrates a bi-directional barbed suture 600 including first end 601a that is attached to a first needle 130a and second end 601b that is attached to a second needle 130b. Needle(s) may be curved or straight, and fabricated from an absorbable or non-absorbable material, such as those described above with respect to the suture, having suitable strength characteristics to introduce and pass the suture through tissue. The needle may be releasable secured to the suture, and may have an eyelet, slot, barb, crimp, or other retention means for securing the suture thereto. It should be understood, however, that any device capable of passing a suture through tissue may be utilized with the suture of the present disclosure.

Referring again to FIG. 1, wound treatment material "W" is disposed within the lumen 108 of the suture body 102. It is envisioned that wound treatment material "W" may be a relatively low viscosity fluid or liquid such that the wound treatment material "W" may freely flow from suture body 102 through channel 120. It is further envisioned that wound treatment material "W" may be provided in a dry state, e.g., in the form of a powder, or dehydrated and provided in a solid or semi-solid state, e.g., in the form of a foam, that hydrates or re-hydrates in the presence of fluid, e.g., physiological fluids.

Barbs 110 are moveable between a first position "a" in which channel 120 is closed and a second position "b" in which channel 120 is open. In embodiments, barbs 110 may be biased in first position "a" to prevent release of the wound treatment material "W" from lumen 108, and moved to second position "b" as barbs 110 grasp tissue (not shown) when suture 100 is passed therethrough. When barbs 110 are moved to second position "b", channel 120 is open thereby allowing the wound treatment material "W" to flow therethrough and/or allowing physiological fluids to enter into the lumen 108 of the suture body 102 to provide moisture to a dry or dehydrated wound treatment material "W".

Wound treatment materials "W" may include, and are not limited to, one or a combination of: adhesives to attach or hold organs, tissues, or structures; sealants to prevent fluid leakage; hemostats to halt or prevent bleeding; and medicaments to provide a therapeutic benefit to tissue.

Examples of adhesives which can be employed include protein derived, aldehyde-based adhesive materials, and cyanoacrylate based adhesives. Examples of commercially available adhesive are albumin/glutaraldehyde materials sold under the trade designation BioGlue™ by Cryolife, Inc., and cyanoacrylate-based materials sold under the trade designations Indermil™ and Derma Bond™ by Covidien LP and Ethicon Endosurgery, Inc., respectively. It is contemplated that any known suitable adhesive may be used.

Examples of sealants, which can be employed, include fibrin sealants and collagen-based and synthetic polymer-based tissue sealants. Examples of commercially available sealants are synthetic polyethylene glycol-based, hydrogel materials sold under the trade designation CoSeal™ by Cohesion Technologies, Inc. and Baxter International, Inc. It is contemplated that any known suitable sealant may be used.

Other examples of adhesives and/or sealants which may form the wound treatment material include: isocyanate terminated hydrophilic urethane prepolymers derived from organic polyisocyanates and oxyethylene-based diols or polyols, including those disclosed in U.S. Pat. Nos. 6,702,731 and 6,296,607, and U.S. Published Patent Application No. 2004/0068078; alpha-cyanoacrylate based adhesives/sealants including those disclosed in U.S. Pat. No. 6,565,840; alkyl ester based cyanoacrylate adhesives/sealants including those disclosed in U.S. Pat. No. 6,620,846; adhesives/sealants based on biocompatible crosslinked polymers formed from water soluble precursors having electrophilic and nucleophilic groups capable of reacting and crosslinking in situ, including those disclosed in U.S. Pat. No. 6,566,406; two part adhesive/sealant systems including those based upon polyalkylene oxide backbones substituted with one or more isocyanate groups in combination with bioabsorbable diamine compounds, or polyalkylene oxide backbones substituted with one or more amine groups in combination with bioabsorbable diisoycanate compounds as disclosed in U.S. Pat. No. 7,129,300; and isocyanate terminated hydrophilic urethane prepolymers derived from aromatic diisocyanates and polyols as disclosed in U.S. Pat. No. 6,894,140.

It is contemplated that the wound treatment material "W" may be a biocompatible sealant and/or adhesive, including, and not limited, to those which cure upon tissue contact, that cure upon exposure to ultraviolet (UV) light, that are multi-component systems (e.g., two-part systems) which are kept isolated from one another and then combined to form the wound treatment material, or any combinations thereof.

Examples of hemostat materials, which can be employed, include fibrin-based, collagen-based, oxidized regenerated cellulose-based and gelatin-based topical hemostats, as well as aluminum alum (i.e., ammonium alum or aluminum ammonium sulfate). Examples of commercially available hemostat materials are fibrinogen-thrombin combination materials sold under the trade designations CoStasis™ by Cohesion Technologies, Inc., and Tisseel™ sold by Baxter International, Inc. Hemostats may include astringents, e.g., aluminum sulfate, and coagulants. It is contemplated that any known suitable hemostat may be used.

Examples of medicaments, which can be employed, include anti-microbials, analgesics, antipyretics, anesthetics, antiepileptics, anti-histamines, anti-inflammatories, antibacterials, antibiotics, cardiovascular drugs, diagnostic agents, sympathomimetics, cholinomimetics, antimuscarinics, antispasmodics, hormones, growth factors, muscle relaxants, adrenergic neuron blockers, antineoplastics, immunogenic agents, immunosuppressants, gastrointestinal drugs, diuretics, narcotics, steroids, lipids, lipopolysaccharides, polysaccharides, and enzymes. It is contemplated that any known suitable medicament having clinic use may be used. In embodiments, medicaments are utilized to promote healing, prevent infection, reduce inflammation, reduce pain, as well as provide other benefits are as known in the art.

In embodiments, the wound treatment material "W" is a hydrogel. A hydrogel may be utilized as an adhesive, sealant, hemostat, or a vehicle for delivery of other wound treatment materials. Hydrogels are materials that absorb solvents (such as water), undergo swelling without discernible dissolution, and maintain three-dimensional networks capable of reversible deformation. A hydrogel may be absorbable or non-absorbable, and can be formed from single or multiple precursors that gel upon activation, e.g., physical or chemical crosslinking, or both. Physical crosslinking may result from complexion, hydrogen bonding, Van der Waals forces, ionic bonding, combinations thereof, or other such physical forces. Chemical crosslinking occurs due to the formation of covalent linkages and may be accomplished by any number of mechanisms, including, free radical polymerization, condensation polymerization, anionic or cationic polymerization, step growth polymerization, electrophile-nucleophile reactions, combinations thereof, and the like. Activation can also be provided in a variety of other ways, such as, for example, changes in pH, ionicity, pressure, temperature, etc.

Precursor(s) may be polymers, macromers, monomers, macromolecules, small molecules, and crosslinkers that are capable of reacting to form a network of crosslinked molecules, e.g., a gel or hydrogel. The precursors may be selected for specific therapeutic uses, for example, adherence, coagulation of blood, dessication, etc.

In embodiments, a hydrogel may be formed from multiple precursors that spontaneously crosslink when the precursors are mixed. In other embodiments, a hydrogel may be formed from a single precursor that crosslinks with endogenous materials and/or tissues. Examples of suitable precursors are described in U.S. Pat. Nos. 6,152,943; 6,165,201; 6,179,862; 6,514,534; 6,566,406; 6,605,294; 6,673,093; 6,703,047; 6,818,018; 7,009,034; and 7,347,850, the entire disclosures of each of which are incorporated herein by reference.

Examples of commercially available hydrogels include hydrophilic hydrogels sold under the trade designation Carbopol® by Lubrizol Advanced Materials, Inc., polyacrylamides sold under the trade designation Cyanamer® by Cyctec Technology, acrylate polymer sold under the trade designation Aquakeep™ by Sumitomo Seika Chemicals Co., as well as Focalseal® by Genzyme, Inc., and Duraseal® by Covidien LP Other known hydrogels include, for example, those disclosed in U.S. Pat. Nos. 5,874,500; 5,514,379; 5,410,016; 5,162,430; 5,324,775; 5,752,974; and 5,550,187.

A hydrogel may be formed within, or prior to, placement in a lumen of a suture of the present disclosure. In embodiments, dry precursors may be placed within a lumen of a suture and activated to form a hydrogel. In some embodiments, activation may occur upon exposure to physiological fluids, and in other embodiments, activation may occur any time prior to placement within tissue. In embodiments, a dehydrated hydrogel may be placed within a lumen of a suture.

A hydrogel may act as a reservoir for another wound treatment material. In embodiments, medicament(s) may be soaked or impregnated into a hydrogel, or mixed with hydrogel precursors. In such embodiments, the hydrogel may provide a controlled release of the medicament. In embodiments, a multi-component adhesive, sealant, or hemostat system may be utilized with a hydrogel. In such embodiments, a first component, such as a catalyst or crosslinker, may be incorporated in the lumen of the suture, e.g., by coating the lumen, and a second component may be incorporated into a hydrogel. It should be understood that adjusting the composition and/or crosslinking density of the hydrogel may regulate the release rate of the second component to control and/or optimize reaction speed.

Exemplary embodiments of methods of forming a barbed suture containing a wound treatment material of the present disclosure are also disclosed herein. Initially, a suture may be formed using any technique within the purview of those skilled in the art, such as, for example, extrusion, molding, casting, and/or spinning. In embodiments, a suture is formed by bi-component spinning. Bi-component spinning may be accomplished by passing two polymer solutions through spinneret orifices and extruding the two polymers into a bi-component fiber having a sheath-core arrangement. It should be understood that the spinneret orifice configuration enables one to obtain different shapes and sizes of core and sheath fibers. After formation of the bi-component fiber, the core fiber is removed thereby leaving a hollow sheath fiber which may be utilized as the suture body.

Prior to, or after, removal of the core fiber, the sheath fiber is barbed. Barbs may be formed by cutting the outer surface of the suture with cutting blades or slitter knives, such as razor slitting blades, rotary shear slitting blades, among others within the purview of those skilled in the art. For example, barbs may be formed by utilizing the cutting method disclosed in U.S. Patent Application Publication No. 2010/0275750, the contents of which are incorporated herein by reference. The suture is barbed deep enough to form channels extending through the outer surface of the suture body to the inner surface.

The lumen is then filled with a wound treatment material. The lumen may be filled in a variety of ways. In embodiments, the wound treatment material may be introduced through one or more channels of the suture in liquid or dry form. In some embodiments, the wound treatment material may be introduced into the lumen by soaking the suture in a wound treatment material until the core is filled. In embodiments in which the wound treatment material is a hydrogel, the suture may be soaked in a prepolymer solution and allowed to cure and/or crosslink. In some embodiments, materials which are soluble in organic solvents, but act as hydrogels in solution, are dissolved in a solvent and soaked into the suture. Thereafter, the solvent is removed. Upon the addition of fluid, such as water or physiological fluids, the polymer will swell but not redissolve.

The barbs are positioned substantially parallel with the longitudinal axis of the elongated body (see, e.g., first position "a" of FIG. 1) to close the channels and prevent release of the wound treatment material therefrom until placement within tissue. Upon introduction of the suture into tissue, the barbs grab tissue as the suture is passed therethrough, and the barbs extend away from the longitudinal axis of the elongated body (see, e.g., second position "b" of FIG. 1) thereby opening the channels. The wound treatment material is then free to flow from the lumen of the suture. In embodiments requiring the addition of fluids to facilitate formation, hydration, or rehydration of the wound treatment material, blood or other tissue fluids may flow into the lumen of the suture through the open channel to provide the necessary moisture to initiate formation, hydration, or rehydration of wound treatment material "W".

Persons skilled in the art will understand that the devices and methods specifically described herein, and illustrated in the accompanying drawings, are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosed devices and methods based on the above-described embodiments. As such, further modifications and equivalents of the invention herein disclosed can occur to persons skilled in the art using no more than routine experimentation, and all such modifications and equivalents are believed to be within the spirit and scope of the disclosure as defined by the following claims.

What is claimed is:

1. A suture comprising:
   an elongated body including an outer surface having a plurality of barbs extending therefrom and an inner surface defining a lumen therethrough, the elongated body including at least one channel extending through the inner surface and the outer surface, the channel defined between an inner surface of one of the plurality of barbs and a cut outer surface of the elongated body; and
   a wound treatment material disposed within the lumen of the elongated body, the barb configured to move between a first position to close the channel and retain the wound treatment material within the lumen and a second position to open the channel and permit release of the wound treatment material therethrough.

2. The suture of claim 1, wherein the channel extends along a portion of a length of the barb.

3. The suture of claim 1, wherein the channel extends along an entire length of the barb.

4. The suture of claim 1, wherein the channel is disposed at a barb angle formed at an intersection of the barb with the elongated body.

5. The suture of claim 1, wherein the wound treatment material is selected from the group consisting of adhesives, sealants, hemostats, medicaments, and combinations thereof.

6. The suture of claim 5, wherein the adhesives include materials selected from the group consisting of protein derived, aldehyde-based adhesive materials, and cyanoacrylate-based materials.

7. The suture of claim 5, wherein the sealants include materials selected from the group consisting of fibrin sealants, collagen-based tissue sealants, synthetic polymer-based tissue sealants, and synthetic polyethylene glycol-based, hydrogel materials.

8. The suture of claim 5, wherein the hemostats include materials selected from the group consisting of fibrin-based materials, collagen-based materials, oxidized regenerated cellulose-based materials, gelatin-based topical materials, and fibrinogen-thrombin combination materials.

9. The suture of claim 5, wherein the medicaments include therapeutic agents selected from the group consisting of anti-microbials, analgesics, antipyretics, anesthetics, anti-epileptics, anti-histamines, anti-inflammatories, antibacterials, antibiotics, cardiovascular drugs, diagnostic agents, sympathomimetics, cholinomimetics, antimuscarinics, antispasmodics, hormones, growth factors, muscle relaxants, adrenergic neuron blockers, antineoplastics, immunogenic agents, immunosuppressants, gastrointestinal drugs, diuretics, narcotics, steroids, lipids, lipopolysaccharides, polysaccharides, and enzymes.

10. The suture of claim 1, wherein the wound treatment material is a hydrogel.

11. A method of making a barbed suture containing a wound treatment material, the method comprising: filling a lumen of a suture with a wound treatment material, the suture comprising an elongated body including an outer surface including a plurality of barbs extending therefrom and an inner surface defining the lumen therethrough, the elongated body including at least one channel extending through the inner surface and the outer surface, the channel defined between an inner surface of one of the plurality of barbs and a cut outer surface of the elongated body, the barb configured to move between a first position to close the channel and retain the wound treatment material within the lumen and a second position to open the channel and permit release of the wound treatment material therethrough.

12. The method of claim 11, further comprising:
    forming the elongated body by spinning a bi-component fiber including a sheath fiber and a core fiber; and
    removing the core fiber.

13. The method of claim 12, further comprising cutting barbs into the outer surface of the elongated body, wherein at least a portion of the cut outer surface forms a channel extending through the outer surface to the inner surface of the elongated body.

14. The method of claim 11, wherein filling a lumen of the suture includes introducing the wound treatment material through the channel of the elongated body.

15. The method of claim 11, wherein filling a lumen of the suture includes soaking the medical device in the wound treatment material.

16. The method of claim 15, wherein the wound treatment material is dissolved in a solvent, and wherein filling a lumen of the suture further includes removing the solvent from the soaked medical device.

17. The method of claim 11, wherein filling a lumen of the suture includes placing hydrogel precursors within the lumen to form a hydrogel therein.

18. The method of claim 17, further comprising impregnating the hydrogel with a medicament.

19. The method of claim 11, further comprising introducing a first component of a multi-component wound treatment material into the lumen of the suture prior to filling the lumen of the medical device, and wherein filling a lumen of the medical device includes introducing a hydrogel containing a second component of the multi-component wound treatment material into the lumen.

* * * * *